US006884591B2

(12) United States Patent
Janigro et al.

(10) Patent No.: US 6,884,591 B2
(45) Date of Patent: Apr. 26, 2005

(54) PERIPHERAL MARKER OF BLOOD BRAIN BARRIER PERMEABILITY

(75) Inventors: Damir Janigro, Cleveland Heights, OH (US); Marc Mayberg, Chagrin Falls, OH (US); Gene Barnett, Gates Mills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/891,023

(22) Filed: Jun. 25, 2001

(65) Prior Publication Data

US 2003/0170747 A1 Sep. 11, 2003

(51) Int. Cl.[7] ........................ G01N 33/53; G01N 33/567
(52) U.S. Cl. ........................ 435/7.1; 735/7.21; 735/7.94
(58) Field of Search ................. 435/7.1, 7.21, 435/7.94; 436/7.1, 7.44, 518, 523, 533, 538, 63, 380, 546, 775; 530/380, 300, 350

(56) References Cited

U.S. PATENT DOCUMENTS

| 5,304,367 A | 4/1994 | Biegon |
| 5,866,347 A | 2/1999 | Swedo et al. |
| 6,117,989 A | 9/2000 | Bandman et al. |
| 6,268,223 B1 | 7/2001 | Cornell-Bell et al. |

OTHER PUBLICATIONS

Missler et al. (Jul. 1, 2000) "Validation and Comparison of Two Solid–Phase Immunoassays for the Quantification of S–100b in Human Blood." Clinical Chemistry 46(7): 993–996.*

Takahashi et al. (Aug. 1, 1999) "Rapid and Sensitive Immunoassays for the Measurement of Serum S100b Using Isoform–specific Monoclonal Antibody." Clinical Chemistry 45(8): 1307–1311.*

Herrmann et al. (2000) "Release of Glial Tissue–Specific Proteins After Acute Stroke." Stroke 31: 2670–2677.*

Biberthaler et al. (2000) "Influence of Alcohol Exposure on S–100b Serum Levels." Acta Neurochir [Suppl] 76: 177–179.*

Erb et al. (May 2000) "S–100 After Correction of Congenital Heart Defects in Neonates: Is it a Reliable Marker for Cerebral Damage?" Ann Thorac Surg 69(5): 1515–1519.*

Tumor Markers in Peripheral Blood of Patients with Malignant Melanoma: Multimarker RT–PCR Versus a Luminoimmunometric Assay for S–100: Berking, Carola et al.; Arch Dermatol Res (1999) 291: 479–484.

Evaluation of Serum Markers of Neuronal Damage Following Severe Hypoglycaemia in Adults with Insulin–Treated Diabetes Mellitus; Strachan, Mark, W., et al., Diabetes/Metabolism Research & Reviews 1999; 15: 5–12.

Outwitting the Blood–Brain Barrier for Therapeutic Purposes: Osmotic Opening and Other Means; Kroll, Robert A. & Neuwelt, Edward A.; Neurosurgery, vol. 42, No. 5; May 1998.

(Continued)

*Primary Examiner*—Elizabeth Kemmerer
*Assistant Examiner*—Christopher James Nichols
(74) *Attorney, Agent, or Firm*—Raymond A. Miller; Pepper Hamilton LLP

(57) ABSTRACT

The present invention relates generally to a peripheral marker or marker of blood brain barrier integrity and methods of using them in the diagnosis, prognosis, and treatment of a variety of diseases. The preferred embodiments of the present invention relate to methods, compositions, kits, and assays useful in determining the integrity or permeability of a blood brain barrier. The various embodiments of the present invention can be used to identify subjects at risk for developing a disease associated with increased permeability of the blood brain barrier, as well as to provide insight on the ability of an agent or agents to pass the blood brain barrier. Preferably, increased levels of S100β protein are used alone or in combination with other markers of diseased state in order to diagnose and prognosticate permeability of the BBB.

29 Claims, 5 Drawing Sheets

OTHER PUBLICATIONS

Autoantibodies in Neuordegenerative Diseases: Antigen–Specific Frequencies and Intrathecal Analysis: Terryberry, J.W. et al., Neurobiology of Aging, vol. 19 No. 3, pp. 205–216, 1998.

Cerebrospinal Fluid Analysis Differentiates Between Relapsing–Remitting and Secondary Progressive Multiple Sclerosis; Jongen, Peter J.H. et al., Neurol Neurosurg Psychiatry 1997; 63:446–451.

S–100 Release in Hypothermic Circulatory Arrest and Coronary Artery Surgery; Wong, Carl H. et al.; Ann Thorac Surg 1999; 67:1911–4.

Serum S100 Protein: A Potential Maker for Cerebral Events During Cardiopulmonary Bypass; Westbay, Stephen et al.; Ann Thorac Surg 1996;61:88–92.

Serum anti–GFAP ad anti–S100 autoantibodies in brain aging, Alzheimer's disease and vascular dementia; Mecocci, P. et al.; Journal of Neuroimmunology 57 (1995) 165–170.

Uncontrolled Reoxygenation by Initiating Cardiopulmonary bypass is Associated with Higher Protein S100 in Cyanotic Versus Acyanotic Patients; Matheis, G. et al.; Thorac Cardiov Surg 2000; 48: 263–268.

* cited by examiner

PERIPHERAL MARKER OF BLOOD BRAIN BARRIER PERMEABILITY

BACKGROUND OF THE INVENTION

The blood brain barrier prevents many compounds in the blood stream from entering the tissues and fluids of the brain. It is generally recognized that nature provides this mechanism to insure a toxin-free environment for neurologic function. A functional barrier in addition to an anatomic barrier, the BBB is of great importance for the maintenance of a constant environment for optimal CNS function. Most metabolic substrates (i.e. sugars and amino acids) are hydrophilic, and traverse the BBB only by specific carrier-mediated transport systems, which are expressed at both the luminal and abluminal sides of BBB endothelial cells. Other molecules traverse the blood brain barrier more freely. As a general rule, the blood brain barrier excludes hydrophilic and allows passage of lipophilic molecules.

Small molecules pass through the endothelial monolayer of the blood brain barrier permeability more freely than large molecular weight compounds. This is in particular true for proteins. In fact, both sites of cerebrospinal fluid ("CSF") formation, the choroid plexus as well as blood brain barrier endothelial cells, allow negligible passage of protein. Macromolecules such as polypeptides/protein, can cross an endothelial cell barrier primarily in three ways: between the cells through cell-cell junctions (paracellular pathway), through the EC, via pores (fused vesicles), or transcellularly via shuttling specific vesicles and receptors. Electron microscopic evidence suggests that macromolecules are shuttled across the endothelial barrier via vesicles.

Unfortunately, a plethora of potentially useful therapeutic agents are blood brain barrier impermeant, severely hampering their potential for aggressive treatment of a broad spectrum of neurological disorders, including brain tumors. The BBB prevents delivery to the brain of compounds, such as chemotherapeutics, pharmaceuticals, neuropharmaceuticals, potential neuropharmaceuticals, and other neurologically active agents, that might otherwise remedy or modify activities, diseases, and disorders in the brain. Interestingly, in many diseased states, the blood brain barrier is less restrictive compared to normal subjects, and this feature allows a window of therapeutic intervention. Diseases in which increased BBB permeability have been reported include neoplasia, ischemia, tumors, hypertension, dementia, epilepsy, infection, multiple sclerosis, and trauma.

The CSF contains proteins but their concentration is much less than that in plasma. In fact, the concentration in CSF is so low that it is customary to regard this compartment as an essentially protein-free fluid, comparable with the aqueous portion of the eye or normal urine. For more than 100 years the analysis of cerebrospinal fluid has been used to monitor, diagnose or detect changes in neurological function in the brain. This approach is based on the concept of a segregated protein content in plasma-vs-brain. When the separation mechanisms that allow the formation of such an outstanding gradient for protein fluxes from the plasma to the brain fail, appearance of serum protein into the CSF will occur. Sampling of cerebrospinal fluid is commonly achieved by invasive techniques, such as "spinal taps", whereby a small amount of CSF is drained usually from the lumbar portion of the spinal cord. Samples can be intra surgically taken from the ventricles or from the sub-arachnoid space in the brain. An obvious limitation of intrathecal detection of blood brain-barrier intactness resides in the fact that sampling of CSF is invasive, and that the sample itself may be contaminated by the procedure. In addition, it has been known for a long time that a gradient in protein content exists from the brain to the lumbar cord. In fact, the concentrations of protein in segments distal to the site of CSF reduction (ventricles) are known to be much higher. It appears that, at least in part, the increased protein in the lumbar compartment of the CSF is due to a combination of protein secreted by parenchymal cells plus a small amount of protein leakage across the blood brain-barrier.

Ongoing or incipient systemic dysfunction of the heart, pancreas, liver or kidney can often be detected with the help of biochemical markers, whose specificity and known kinetics permit diagnostic and prognostic evaluation. The complexity of CNS function and the multiple kinetic parameters involved in bio-distribution across the blood brain barrier and within the brain parenchyma imposes a considerable burden for the interpretation of putative biochemical markers present in serum or cerebrospinal fluid. While changes in the composition of cerebrospinal fluid are commonly used to diagnose a variety of neurological diseases, the invasiveness of the procedures involved greatly decrease their usefulness It would be useful to have a predictable and reliable peripheral marker of blood-brain barrier integrity in order to monitor the neurological status of a subject and to predict outcome and/or to adjust the therapy.

SUMMARY OF THE INVENTION

The present invention is directed to a peripheral marker, used alone or in combination with other markers, which is indicative of the permeability of the blood brain barrier.

The present invention is based on monitoring and measuring markers of blood brain barrier permeability, particularly S100β as a peripheral marker, alone or in combination with other markers of disease or neuronal damage. Preferably, levels of S100β are determined and compared with a control sample (e.g., levels found in a normal population); changes above these baseline values being indica of blood brain barrier dysfunction or permeability. S100β protein may also be observed as an indicator of brain damage, along with other markers of neuronal distress.

The embodiments of the present invention provide: methods; compositions; and kits for the diagnostic and prognostic evaluation of an opening in the BBB. These embodiments are particularly useful in the identification of subjects possessing a predisposition to passing or preventing agents from passing the BBB, and for monitoring patients undergoing treatment involving the integrity of the BBB, based on the detection of increased levels of S100β protein expression in a blood derived sample of subjects.

In one embodiment, the present invention provides for a method for diagnosis of blood brain barrier permeability by means of detecting levels of S100β protein in a sample of biological fluid, preferably a blood sample, from a patient and comparing the level of protein detected in the sample with the level of protein detected in a control. Additionally, the method for diagnosis can include detecting the levels of markers of neuronal distress, suitable markers being, for example, NSE and GFAP, and albumin. The diagnosis of BBB permeability can be made independent of neuronal distress. The level of S100β protein detected in the sample as compared with the level detected in the control is an indication of BBB permeability. The sample obtained from a patient is evaluated based upon the level of BBB permeability. The S100β protein is preferably detected using an immunoassay, such as an immunoprecipitation assay.

Another embodiment of the present invention provides for a method of diagnosing a patient that includes identifying a first elevated level of S100β in the blood of a patient and identifying a second elevated level of S100β in the blood of the patient. The second elevated level is expected to be statistically greater than said first elevated level of S100β. In this embodiment, the presence of a statistically relevant first elevated level of S100β is indicative of BBB opening, and the presence of both the first and second elevated levels is indicative of neuronal damage and blood brain barrier opening.

Another embodiment of the present invention provides for detecting onset of neuronal distress in a patient by identifying elevated levels of S100β protein in the biological fluid, such as blood or serum. Additionally, the method for detection can include detecting the levels of markers of neuronal distress, with suitable markers including NSE, GFAP and MBP. The level of S100β protein detected in the sample as compared with the level detected in the control is an indication of BBB permeability, while the other markers are indicative of neuronal distress. The sample obtained from a patient is evaluated and scored based upon the level of BBB permeability. The S100β protein is preferably detected using an immunoassay, such as an immunoprecipitation assay.

Another embodiment of the present invention provides for a method of detecting BBB integrity by contacting a serum sample derived from a subject with an antibody under conditions such that a specific antigen-antibody binding can occur, and detecting immunospecific binding of S100β protein in the serum sample, where the presence of S100β indicates the degree of BBB permeability.

Another embodiment of the present invention provides for detecting a brain tumor in a patient by identifying elevated levels of S100β protein in the patient's biological fluid, such as blood or serum. Additionally, the method for detection can include detecting the levels of other markers of neuronal distress. The level of S100β protein detected in the sample as compared with the level detected in the control is an indication of BBB permeability and thus either a primary tumor or metathesis of a tumor into the brain. In this embodiment the sample that may be obtained from a patient is evaluated and scored based upon the level of BBB permeability in a stimulant.

Another embodiment of the present invention provides for detecting brain tumorogenesis in a patient by identifying elevated levels of S100β protein in the patient's biological fluid, such as blood or serum. The level of S100β protein detected in the sample as compared with the level detected in the control is an indication of leakage of S100β into the blood. The sample obtained from a patient is evaluated and scored based upon the level of BBB permeability.

Another embodiment of the present invention provides for a method of detecting re-occurrence of a primary tumor by screening a patient predisposed to re-occurrence of a primary tumor for elevated S100β protein in the patient's biological fluid, such as blood or serum.

Another embodiment of the present invention provides for a method of detecting an opening in the BBB in patients who do not have neuronal damage by detecting S100β.

Another embodiment of the present invention provides for a method of determining whether a tumor is metastatic or primary by detecting a cancer marker and determining levels of S100β in a patient's blood.

Another embodiment of the present invention provides for a method of treating a patient in need thereof with a therapeutic agent. The method includes the steps of administering an agent which opens the BBB, verifying elevated levels of S100β protein in the blood, administering the therapeutic agent, closing the BBB, and confirming that the BBB is impermeable by detecting reduced levels of S100β protein in the blood. These steps are employed preferably where a patient suffers from a disease, such as neoplasia, ischemia, hypertension, dementia, epilepsy, infection, multiple sclerosis, and trauma. The therapeutic agents that may be employed include chemotherapeutics, pharmaceuticals, neuropharmaceuticals, potential neuropharmaceuticals, and other neurologically active agents.

Another embodiment of the present invention provides for a method for delivering a compound from the bloodstream to the brain. The method includes applying an agent which opens the BBB and determining the level of S100β in the blood and, when the S100β in the blood is elevated, introducing the agent into the blood stream while the BBB is open. The compound is admitted into the patient's bloodstream at least in the vicinity of the selected location. The compound may be a contrast agent, a neuropharmacologic agent, a neuroactive peptide, a protein, an enzyme, a gene therapy agent, a neuroprotective factor, a growth factor, a biogenic amine, a trophic factor to any of brain and spinal transplants, an immunoreactive protein, a receptor binding protein, a radioactive agent, an antibody, and a cytotoxin. Preferably, determination of the level of S100β is repeated over a course of treatment to determine efficacy of the treatment.

Another embodiment of the present invention comprises assays developed to detect the level of S100β proteins in a subject's serum sample. Such assays include immunoassays wherein the S100β proteins are detected by their interaction with anti-S100β specific antibodies. For example, S100β antibodies or fragments of antibodies maybe used to quantitatively detect the presence of S100β proteins in a serum sample.

The embodiments may also involve the use of the S100β protein antigens in immunoassays designed to detect the presence of serum autoantibodies to the S100β protein antigens. Such immunoassays can be utilized to determine the permeability of the BBB. In accordance with the invention, measurement of S100β levels in a subject's serum can be used for the early and ongoing diagnosis of the status of the BBB. Moreover, the monitoring of S100β levels can be used prognostically to stage progression of the disease or the treatment.

Another embodiment of the present invention provides for a kit for diagnosis and prognosis of blood brain barrier integrity in a subject. The kit includes a component for detecting a peripheral marker of blood brain integrity. The component is utilized for the purpose of detecting the presence S100β protein in a blood sample, where elevated levels of S100β protein is indicative of BBB opening independent of brain damage. The kit additionally includes a component for detecting levels of markers of diseased states to correlate the diseased state with opening of the BBB. The component for detecting S100β protein is preferably an anti-S100β antibody, where the antibody is monoclonal. The anti-S100β antibody contains a label, which may be a radioactive, fluorescent, colorimetric or enzyme label. The kit provided for in this embodiment also contains a labeled second antibody that immunospecifically binds to the anti-S100β antibody. The marker for disease is a marker for neuronal distress and a marker for cancer, that can be NSE or GFAP. The types of cancer for which the marker may be applied include breast cancer, colon cancer, brain cancer, and lung cancer.

Another embodiment of the present invention provides for a kit for detection of brain damage. The kit of this embodiment contains a first and second component. The first component, which determines permeability of the blood brain barrier, is used for detection of S100β protein in a blood sample shortly after injury (on the order of minutes to hours). The second component, which determines neuronal distress, is used for detecting levels of markers of neuronal distress.

Another embodiment of the present invention provides for pre-packaged diagnostic kits, which will be conveniently used in clinical settings, to diagnose or monitor patients with impaired BBB integrity. The kits will also be utilized to monitor the efficacy of compounds used for treatment of diseases associated with BBB integrity or lack thereof.

In a specific embodiment of the invention described herein, an increase in the level of specific S100β proteins was detected in serum samples derived from subjects with impaired BBB function. The finding that levels of S100β proteins are increased in serum of subjects who have an openings in the BBB provides a basis for development of diagnostic and prognostic methods as well as methods for differentiating between the efficacy of various therapeutic treatments for diseases associated with the integrity of the BBB.

Also disclosed are possible uses of this observation to predict incipient neurological disease, adverse reactions to medical treatment and efficacy or toxicity of drugs administered systemically.

Additional aspects and applications of the present invention will become apparent to the skilled artisan upon consideration of the detailed description of the invention, which follows.

DETAILED DESCRIPTION OF THE INVENTION

Figure 1:
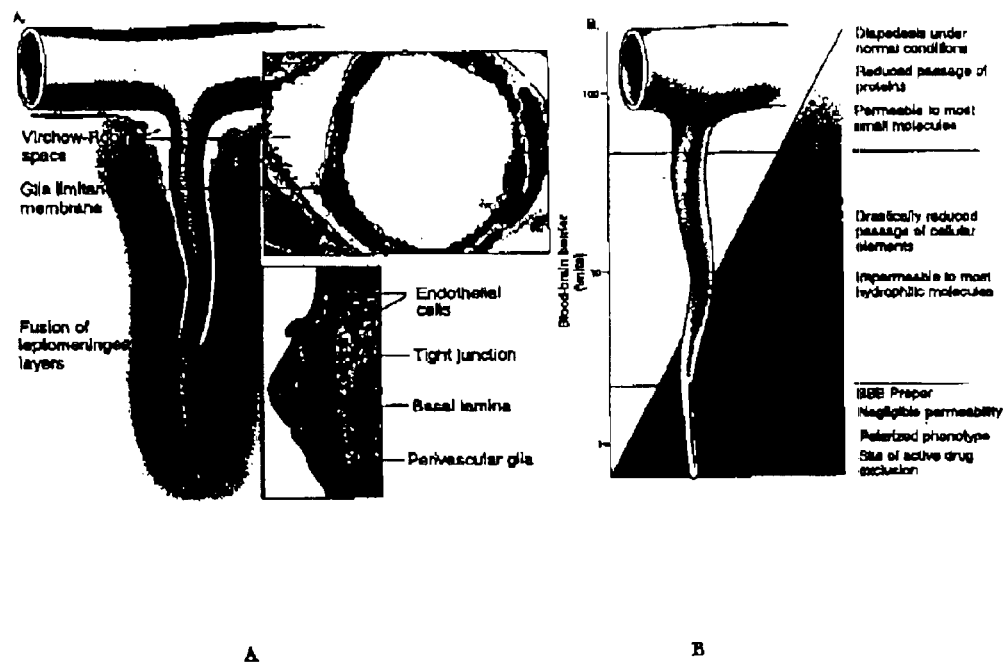
FIG. 1A is a diagrammatic representation of the mammallian BBB and its anatomical relationship to the brain parenchy.
FIG. 1B illustrates a proposed blood brain barrier score in accordance with embodiments of the present invention.

Before the various embodiments of the present invention are described, it is to be understood that this invention is not limited to the particular methodology and protocols described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to the "antibody" is a reference to one or more antibodies and equivalents thereof known to those skilled in the art, and so forth.

By "sample" it is meant a volume of fluid or tissue, such as blood or CSF, but preferably blood which is obtained at one point in time. A sample can be as little as 2.5 mL (or less) taken from the subject. Further, as will be discussed in detail below, all the markers can be measured with one assay device or by using a separate assay device for each marker, in which case aliquots of the same fluid sample can be used or different fluid samples can be used. The analyses should be carried out within some short time frame after the sample is taken, e.g., within about one-half hour, so the data can be used to prescribe treatment as quickly as possible.

The terms "above normal" and "above threshold" are used herein to refer to a level of S100β that is greater than the level of S100β observed in normal individuals, that is, individuals who are not undergoing an event, i.e. an opening of which may be ischemic, mechanical or infectious. These terms contemplate a level that is significantly above the normal level found in individuals. The term "significantly" refers to statistical significance. The assay method by which the analysis for the S100β protein is carried out must be sufficiently sensitive to be able to detect the level of the marker which is present over the concentration range of interest and also must be highly specific. Ranges of S100β should be detectable from about 0.001 µg/L to about 1 mg/L of blood, with 0.01 µg/L to 800 µg/L of blood being even more preferred.

The assay devices used according to the invention can be arranged to provide a semiquantitative or a quantitative result. By the term "semiquantitative" is meant the ability to discriminate between a level which is above the elevated marker protein value, and a level which is not above that threshold.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference. Nothing herein is to be construed as an admission that the invention is not entitled to antedate such disclosure by virtue of prior invention.

Functional significance of S100β proteins. S100 proteins bind calcium in the EF-hand domain but react with target proteins by means of cysteine residues, and by a region of 13 amino acids, called the linker region. S100A1 has one reactive cysteine residue while S100β has two. S100β has also two zinc $Zn^{2+}$ binding sites which are separated from the calcium binding sites. The binding of $Ca^{2+}$ or $Zn^{2+}$, or both, to their respective binding sites changes the reactivity of the S100β molecule, to target proteins (e.g., protein kinases) by means of conformational changes in the protein. The affinity of S100β proteins for $Ca^{2+}$ is therefore an important parameter, which can be influenced through the binding of $Zn^{2+}$ (increasing the affinity) or $K^+$ (decreasing its affinity) in several family members.

Target for S100β include a wide variety of cytoplasmic proteins with calcium-dependent actions: as a result, S100β proteins can exert pleiotropic effects in the cell. One major system influenced by S100β activation involves protein kinases, a broad and heterogeneous family of enzymes that phosphorylate other proteins and thereby play a central regulatory role in many cellular processes. The protein kinase twichin is involved in the regulation of muscle contraction and is associated with myosin. Calcium bound-S100A1 acts as a specific and potent activator of twichin and may also impact on cytoskeletal structure. There is also a possibility that gap junctions could also respond to variation in S100 protein level. Gap junctions are important in electrical conductivity of cardiac muscle. Recently propanolol was found to bind to S100β protein in cardiac muscle and to alter their conformation.

Inflammatory cells, especially neutrophils and dendritic Langherans' cells contain abundant S100β but the functional significance of S100β in these cells is unknown. Macrophages also contain S100β proteins, and evidence suggests that S100β proteins can be secreted by macrophages into the extracellular space where they could have antimicrobial, cytostatic, chemotactic, or migration-inhibition activities.

A desirable property of a blood brain barrier marker is its virtual absence from the systemic circulation. However, given the above mentioned non-neuronal, non-CNS distribution of S100β, it may appear that this condition is not fulfilled. However, in spite of its documented expression in systemic cells, S100β is conspicuously low in serum of normal subjects, suggesting that its non-CSF distribution must be intracellular and that little or no release in the systemic circulation occurs physiologically.

S100 in the nervous system. S100β is localized primarily in glial cell cytoplasm and processes, with no specific staining observed in glial cell nuclei, erythrocytes, or neuronal cells. Reported data shows the distribution of S100β in the human nervous system detected by immunocytochemical method. The number and staining intensity of S100β positive astrocytes cells is similar in both the molecular and polymorphic layers of the hippocampus were described. In the occipital cortex, for all layers, the numbers of S100β positive astrocytes were about twofold higher than those found in the hippocampus and entorhinal cortex.

Furthermore the astrocytic localization of the protein is documented wherein cells expressing immunoreactivity for the monocarboxilate transporter MCT1 are astrocytes. Those cells also co-express strong immunoreactivity for S100β.

In the normal brain, the S100β gene undergoes complex positive and negative transcriptional regulation that provides precise control of the level of S100β protein. S100β has been shown to be neuroprotective during glucose deprivation, but may be neurotoxic if overexpressed, triggering apoptosis. Interestingly, nanomolar concentrations of S100β act both as growth and differentiation factor, whereas micromolar concentrations are necessary for induction of apoptosis. Gliosis and neurite proliferation have been shown to occur in transgenic mice overexpressing S100β. S100β is increased in activated astrocytes surrounding degenerative plaques in Down's syndrome and Alzheimer's disease, but given the dual neuroprotective-neurotoxic effects of S100 in the CNS, a possible etiologic link is speculative.

Understanding the anatomical features and function off the blood brain barrier provides insight into the vast applicability and importance of the present invention. The BBB is a continuous, tight-junctioned, endothelial cell layer. The endothelial layer actually consists of two separate cell membranes, one on the inside of the vessels (luminal) and one on the outside (abluminal) separated by 300–500 nm of thick cytoplasm. The endothelial cells, however, are only one part of a "BBB complex", which consists of astrocytes, pericytes, microglia, and neurons. All of these cell types play a role in the induction and maintenance of the specialized BBB endothelium. The microvascular endothelium shares a common basement membrane with astrocytes and pericytes. Beyond the basement membrane in parenchymal vessels of the brain lies a close investment of end feet from neuroglial cells, predominantly astrocytes. Astrocytes and their processes invest more than 90% of endothelial capillaries and their end feet are projected tightly around the endothelial cells. Therefore, the glial end feet are a natural candidate to mediate a communication link between neurons and capillaries. Thus, for this reason, astrocytic proteins are candidates for a role of peripheral markers of blood brain barrier integrity, inasmuch it is only when the BBB is breached that these proteins extravasate into the plasma compartment. Recent evidence has shown that shear stress promotes the expression of numerous genes involved in various aspects of endothelial cell function. Precisely how flow or lack of flow contributes to brain endothelial cell function is presently unknown. Indirect evidence suggests that flow is an initial step of endothelial differentiation, suggesting that flow cessation or changes on flow pattern (e.g., as seen during ischemia reperfusion or hypo-hypertension) may impact BBB integrity or tightness. It is also unknown whether changes in EC induced by flow may affect neighboring glia, and if these changes may affect expression of astrocytic proteins that may be detected in plasma. Pericytes also limit transport across the BBB along with macrophages through the ability to phagocytes compounds which have crossed the endothelial barrier and therefore act as a second line of defense just behind of the endothelium. The possibility exists that pericyte-specific proteins may become useful markers of BBB function, owing to their proximity to the plasma compartment and their strategical location of the endothelial-brain interface. As can be seen in FIG. 1A, not all the blood vessels in the brain constitute a blood brain barrier. Only capillary vessels are endowed with a full-blown BBB phenotype. In FIG. 1A, a diagrammatic representation of the mammalian BBB and its anatomical relationship to the brain parenchyma is illustrated. As can be seen in FIG. 1A, large pial vessel penetrate the brain parenchyma from the subarachnoid space leaving a space (VR space) filled with CSF. This space progressively vanishes, owing to the fusion of the pia mater with the vessel wall. The electron microscopy inserts show two distinct levels of penetrating vasculature. Note that precapillary vessels are formed by juxtaposition of vascular smooth muscle and endothelial cells, while at the capillary level EC are engulfed by astrocytic endfeet. Understanding the BBB phenotype is important for a host of reasons. One important aspect of the phenotype is that it is believed that primary tumors, and more particularly the vessels that feed these tumors, do not have full blown BBB phenotype. Thus the "leakage" of S100β from a primary brain tumor allows for differentiation and location of the brain tumor. Accordingly in an embodiment of the present invention, differential diagnosis of tumor types is provided. For example, if a primary brain tumor undergoes any type of angiogenesis or vascular growth, the leakage of S100β from these leaky vessels into the blood provides evidence of the locale and type of tumor (i.e., in the brain). Conversely, an indicator of a non-primary tumor type coupled with release of S100β into the blood stream provides evidence that the cancer has metastasized and penetrated or permeated the blood brain barrier.

FIG. 1B suggests a "BBB score" which provides for a score associated with gradients in BBB function (or tightness) that exists along brain vessels. Again, note that the BBB proper is present only at the capillary level. This "BBB score" may provide a useful diagnostic tool in grading the permeability of the BBB. Vessels of increasing diameter have comparably increasing levels of leakiness and thus superficial vessels of large diameter are the leakiest while penetrating pial vessels and descending penetrating vessels tend to have an intermediate barrier function. Since most animals, including vertebrates, have some form of a barrier separating their blood circulation from the brain or the central nervous system, it has been speculated that profound evolutionary pressure existed to create such a complex organ.

Cellular mechanisms of altered BBB permeability. Our understanding of the cellular or molecular mechanisms that initiate changes in BBB permeability is limited. Several vasoactive compounds, which include bradykinin, complement 3a, ATP, histamine and serotonin from mast cells, interleukines, arachidonic acid and its metabolites, interferon alpha and beta, prostaglandin, and tumor necrosis factor, have all been shown to alter BBB permeability. While the fact that a number of chemical triggers may interrupt the continuity of endothelial tight junctions, the cellular source of these mediators is not always clear. Most of the aforementioned effectors of BBB disruption may be released by perivascular glia, thus opening a window for molecular communication between brain and plasma. It is in fact likely that changes in brain homeostasis (e.g., during ischemia), accumulation of plaques (Alzheimer's disease), release of interleukines (inflammation) may all translate into reactive astrocytic changes that in turn promote opening of the BBB and cause appearance in plasma of molecules normally segregated into the CNS. In addition, these extravasatory molecules may be synthesized ex novo as a consequence of the disease itself.

In addition to soluble molecular signals, the BBB responds to and is traversed by cellular elements. Under normal conditions, the tightness of the BBB is a serious hindrance to the entry of both immunocompetent cells and specific antibodies, which are necessary if the immune system is to attack infections agents or abnormal autologous cells undergoing uncontrolled proliferation in the brain. The highly specialized tight endothelium isolates the brain from immune surveillance and allows only a few mononuclear cells (activated T cells) to migrate into the CNS. Therefore, the low expression of major histocompatibility complex antigens, the low number of antigen-presenting cells, and the fact that the CNS is not drained by a fully developed lymphatic vasculature, makes the brain an "immunoprivileged" site. However, when inflammation does occur, there is extensive leukocyte migration occurs into the brain. Both brain endothelial cells and astrocytes can act as antigen presenting cells in order to facilitate the entry of T-lymphocytes and antibodies. The BBB itself plays an active role in the mediation of this neuroimmune response, either by the production of inflammatory mediators or by expression of adhesion molecules. Since activated immunocompetent cells are known to secrete a number of proinflammatory signals, it has been proposed that these molecules may act as indicators of BBB function. In any case, passage of cells across the BBB causes sufficient disruption of the endothelial layer to promote extensive passage of proteins or other macromolecules, thus facilitating the peripheral detection of CNS components.

The BBB is not a static organ, and numerous factors affect BBB permeability. In the early 1960s, Majno and Palade showed that after exposure of tissue to histamine, carbon particles injected into the blood compartment entered the parenchyma (tissue) selectively via post capillary venule endothelial cells ("ECs"). Moreover, gaps were occasionally seen. In a subsequent study, Majno et al observed that the nucleus of these ECs had a wrinkled appearance and postulated that contraction of the EC was the basis for the increased extravasation of macromolecules. This insightful observation is supported by more recent findings and constitutes the rationale for "osmotic opening" of the BBB.

A functional barrier in addition to an anatomic barrier, the BBB is of great importance for the maintenance of a constant environment for optimal CNS function. Most metabolic substrates (i.e. sugars and amino acids) are hydrophilic, and traverse the BBB only by specific carrier-mediated transport systems, which are expressed at both the luminal and abluminal sides of BBB endothelial cells. There are marked apical/basal differences in the distribution of carriers and enzymes, which distinguishe the specialized BBB endothelium from peripheral endothelium. By attaching therapeutically active macromolecules to agents that bind these specialized transport systems, the macromolecules may be taken up, transported through the endothelial cells, and ultimately released on the abluminal side of the vessel (brain parenchyma). Owing to the close interaction of perivascular glia and brain capillary endothelial cells, it is commonly accepted that the "blood brain barrier organ" is constituted not only by endothelial cells, but glial end feet as well. Current understanding of the mechanism of neuro-immunological interactions of specialized cells with the blood brain barrier has also suggested involvement of both perivascular pericytes and microglia as active components of the blood brain barrier. Under neuro-pathological conditions, both perivascular astrocytes and blood brain barrier endothelial cells undergo significant changes.

Clinical implications of the "sick BBB" and its relationship to markers of brain damage. Substantial progress has been made in the understanding of the pathophysiology and mechanisms involved in the attenuation of BBB permeability. In many diseases that affect the brain, the cerebral endothelium plays an active part in the disease process with the BBB becoming disrupted, or modified, in such a way there is a dramatic increase in vascular permeability. Theoretically, several ways exist in which various molecules can pass the endothelium. These include intercellular routes, vesicular transport, or direct transcellular penetration through damaged endothelium. BBB dysfunction may be a cause or consequence of a particular disease process. Diseases in which increased BBB permeability have been reported include neoplasia, ischemia, hypertension, dementia, epilepsy, infection, multiple sclerosis, and trauma. The effect of a disease on BBB function will secondarily affect the cerebral blood flow and vascular tone in the brain, which further influences transport across the BBB. Besides the effects of increased vascular permeability on the brain parenchyma, a question of great significance is whether, in certain neuropathological conditions, the BBB disturbance constitutes the main pathogenic factor itself, which then triggers a sequence of events molding the final pathological state.

In addition to the invasive techniques routinely used in current clinical practice, several monitoring techniques have been developed to measure brain damage or neuronal distress by measuring plasma levels of various CNS proteins, including S100$\beta$ protein; glial fibrillary acidic protein (GFAP); neuron specific enolase (NSE); and the myelin basic protein (MBP).

Figure 2:
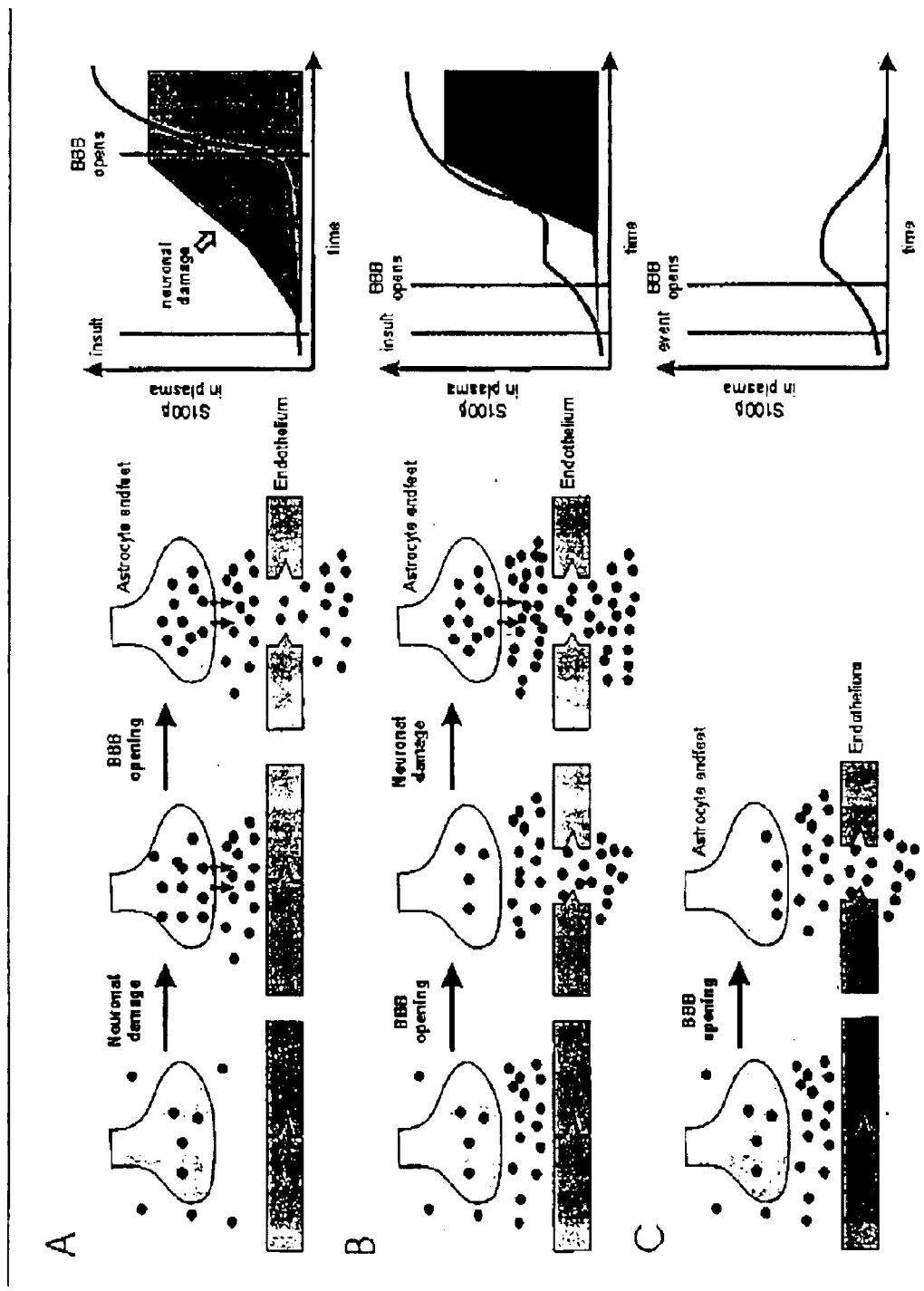
FIG. 2A through FIG. 2C illustrate the relationship between S100β and neuronal damage, and the dynamics of S100β protein across the blood brain barrier.

While not wishing to be bound by theory, FIG. 2 illustrates a proposed temporal and typographic relationship between S100β and its dynamics across the blood brain-barrier (BBB). Three different scenarios are presented: Scenario (a) depicts changes occurring when neuronal damage precedes BBB opening; Scenario (b) depicts BBB opening preceding neuronal damage; and Scenario (c) depicts BBB opening occurring in the absence of neuronal damage. Note that if S100β is released as a consequence of neuronal damage and BBB opening follows this event, measurable neuronal damage will precede temporal increases in S100β availability in plasma. If, conversely, BBB opening precedes neuronal damage the opposite will be true. Note however, that under the latter conditions two separate peaks of S100β concentration in plasma are expected, one due to leakage across the BBB and an additional peak caused by massive release of S100β by suffering neuronal cells and glia. This allows for an embodiment of the present invention, wherein S100β is used to stage neuronal distress. This embodiment includes identifying a first elevated level of S100β in a blood sample of a subject and a second elevated level of S100β in a subject. Identification of the first elevated level of S100β is indicative of BBB permeability and identification of the second elevated level of S100β is indicative of neuronal damage, if it exists. Of course the neuronal damage may also be indicated and detected by other markers of neuronal distress, if desired.

Importantly, extravasation of S100β in plasma also occurs in the absence of neuronal damage, as presented in Scenario (c). Under these conditions, it is assumed that S100β is readily available in the cerebral spinal fluid but not in plasma under normal conditions. Following opening of the BBB, even in the absence of any damage, S100β extravasates and becomes available in the plasma compartment.

Figure 3:
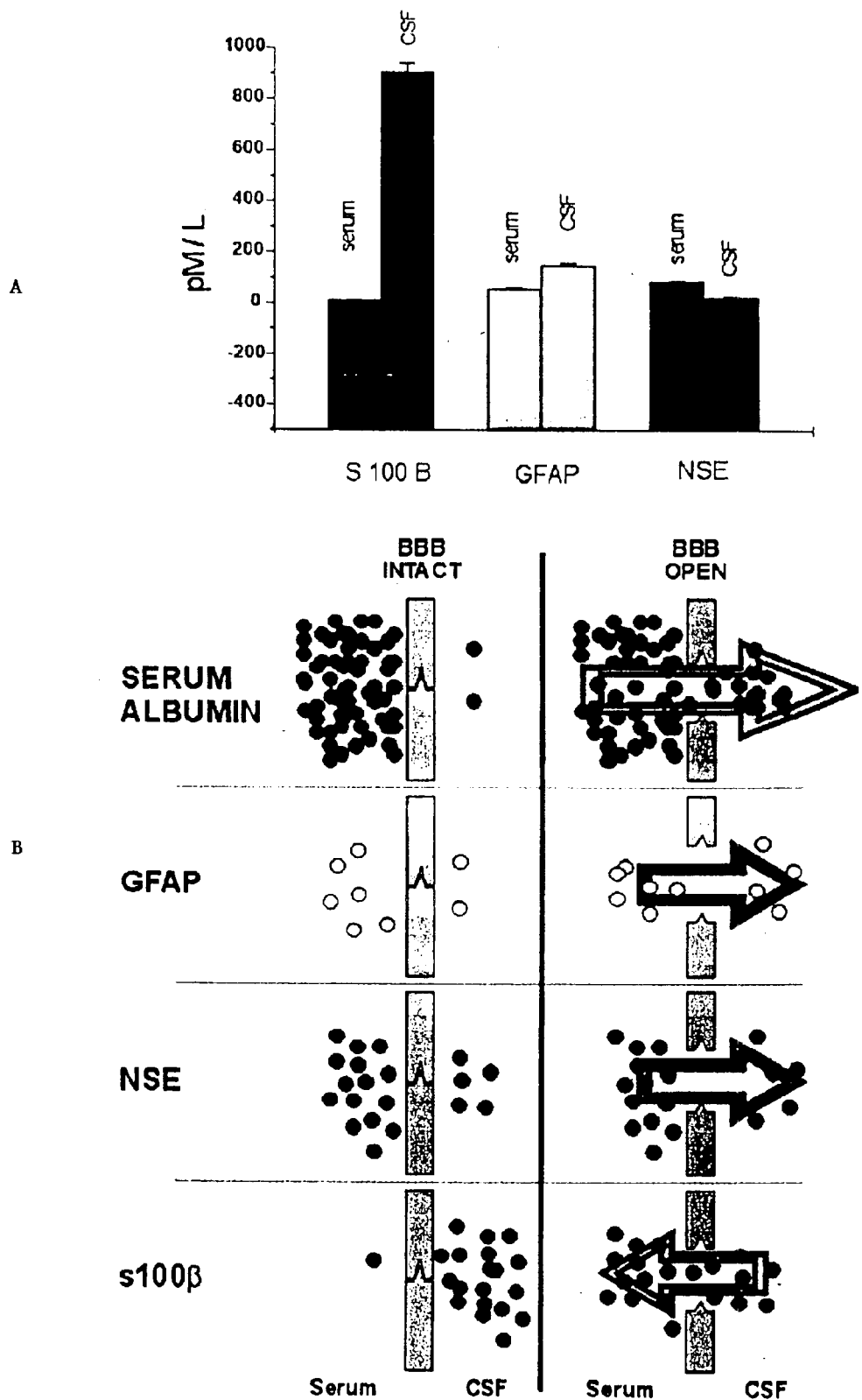
FIG. 3A summarizes concentrations of S100β, GFAP, and NSE in serum and CSF.
FIG. 3B illustrates the predicted fluxes of various proteins present in serum and CSF.

As is particularly illustrated in FIG. 3, S100β would appear to be a particularly viable candidate as a marker of blood brain-barrier function. The upper histogram (FIG. 3A) summarizes concentrations of S100β, GFAP, and NSE, in serum and cerebral spinal fluid (CSF) as derived from the literature. Note that in the case of S100β, CSF concentrations are under normal conditions much larger than those found in serum. In the case of GFAP and NSE, serum and CSF levels are almost identical. FIG. 3b shows the predicted fluxes of various proteins present in plasma or brain. Serum albumin is normally concentrated in plasma and virtually absent from the CSF. Upon opening of the BBB, it is expected that serum albumin will extravasate into the CSF compartment. This extravasation of protein into the central nervous system (CNS) constitutes the basis of invasive methods for determination of BBB leakage (e.g. spinal tap). Note that a similar theoretical framework is at the basis of the use of contrast agents to visualize BBB leakage following intravenous injection (Gadolinium). In the case of GFAP opening of the barrier would appear to promote a small influx from the plasma into the CSF. Because GFAP concentrations are virtually identical across the BBB, it is not expected that these protein levels will change significantly when the barrier is breached. Similar considerations apply in the case of NSE. S100β, in contrast, is predominantly located in the CSF. Upon opening of the BBB this protein is expected to appear into the serum, allowing for peripheral detection of BBB function in absence of neuronal damage.

A peripheral marker of BBB leakage or permeability should include most of the following properties: plasma levels in control subjects must be exceedingly low or undetectable; similarly, under normal conditions CSF levels must be constant or, ideally, low; significant increases of the marker's concentrations must occur at early stages of neuronal distress; CSF changes must be reflected by comparable changes in plasma levels. Of the candidates, S100β would appear to be the best peripheral marker in reflecting BBB permeability and/or neuronal damage with regard to those characteristics. Importantly S100β also appears to be the preferred marker in indicating blood brain barrier permeability without or before neuronal damage.

Distinguishing between BBB opening and neurological damage is not trivial and bears substantial clinical relevance. For example, in acute CNS disturbances such as ischemic stroke, the delayed process leading to irreversible neuronal cell death offers a window of therapeutic opportunity. If, as suggested by numerous studies BBB openings occur early after the initial arterial occlusion, one may envision the unveiling of unique opportunities to administer drugs that are normally BBB impermeant (e.g., "nerve growth factors"). Since it is likely that these openings may be of unpredictable duration in any given specific patient, a peripheral non-invasive test consistent with the overall management of these patients may be of extreme therapeutic usefulness. In chronic neurological diseases (e.g., multiple sclerosis), BBB openings may have both therapeutic and etiologic significance, since a correlation between severity of symptoms and BBB function has been suggested and given the fact that promising therapies based on brain-derived proteins have failed largely because of poor penetration of these proteic compounds across the BBB.

Neuronal vs. glial/endothelial damage. The term "brain damage" has often been used as a synonym of "neuronal damage" or neuronal cell death. This is understandable given the fact that neurologic deficits attributable to neurological disease are almost exclusively imputable to either neuronal loss or dysfunction. Investigations on the mechanisms of neuronal cell death soon revealed the perhaps not surprising fact that neuronal sensitivity to insult is region— and disease-specific. Thus, it appears ischemic insult will selectively affect the CA1 region of the hippocampal formation, leaving the neighboring dentate gyrus and CA3 practically intact. In contrast, damage resulting from epileptic seizures is more prominent in CA3 hippocampal subfield. In addition to these patterns of specificity, it has also been observed that neuronal cell death does not occur concomitantly to the insult but is rather the result of a sequence of delayed events. This is particularly true in acute insults such as ischemia where a therapeutic window for neuroprotective intervention exists. In chronic/progressive neurological diseases changes occur at an even slower rate, and usually follow rather predictable patterns (e.g., multiple sclerosis).

How non-neuronal cells participate, react, or promote repair of neuronal damage remains largely unknown, but again region-specific and distinct temporal patterns exist. Whether changes occurring in non-neuronal cells may actually cause neuronal damage is a concrete possibility that has received surprisingly little attention. This is particularly evident in the case of cerebrovascular diseases where the clinical reality and current approaches are focused on changes occurring in cerebral vessels, but nonetheless most basic science investigations have focused on yet fruitless interventions at the synaptic level. Furthermore, in the case of brain tumors, the etiologic component is most commonly glial but the measurable deficits are frequently imputable to changes in neuronal function. Finally, in chronic disease such as multiple sclerosis, an inflammatory or autoimmune mechanisms seems to account for the widespread loss of neurons in the CNS.

As far as endothelial cells constituting the blood brain barrier are concerned, it appears that most neurological diseases are accompanied by some change in BBB permeability. Whether these changes actually precede (or even cause) the damage is presently unclear. The fact remains that the concomitant presence of a defective BBB shielding and neuronal cell damage makes it extremely difficult to separate these two phenomena. It is thus possible that some of the putative peripheral markers of neuronal damage are also direct measurements of BBB integrity.

Detection of markers in peripheral blood: S100β. Even if a peripheral marker of brain or BBB damage fulfills the criteria listed, it is necessary to consider issues related to the peripheral marker's metabolism and on the analytical methods to assay serum concentrations of the marker itself. The metabolic fate of S100β is unknown but there is evidence to believe that metabolism and elimination follow the same pattern as for other low molecular weight proteins. Filtration through the glomerular membrane is followed by reabsorption and degradation in the proximal tubules, in normal physiological condition the half life has been estimated to be 110 minutes. The exact knowledge of reference values for both serum and CSF concentration are necessary to understand the time course of S100β during pathological conditions and as an early predictor of neuronal damage. According to an earlier report, plasma S100β concentration in healthy adults is age and sex independent. The median concentration for men is about 0.055 μg/L, and for women is about 0.048 μg/L; plasma concentration of S100β decreased slightly with aging. No evidence was found suggesting that age and sex-corrected reference values need to be established for measurements of S100β concentrations in the blood of adults. Such may be not the case for determinations of S100β concentrations in children, since animal studies indicated that S100β concentrations in the brain change substantially during postnatal development. The S100β CSF concentration in healthy adults was found to be sex dependent, and significant differences between men and women (mean values 1.9 versus 1.5 μg/l) have been reported. CSF levels increased with age in both sexes, but this relationship appears to be less pronounced in women. There are several explanations for an age related increase in S100β protein in CSF: (a) the age dependency reflects increasing myelin loss with age; (b) the S100β protein concentrations in the cells increase with age, whereas the turnover of the cells remains constant; (c) the increase could be a result of increased half-life attributable to a reduced CSF bulk flow at older age; or (d) The BBB may become leakier in aging individuals, as reflected by changes in CSF composition that occur in otherwise healthy elderly volunteers.

In addition to exhibiting such a complexity, the S100β appears to be a target of altered gene regulation by pharmacological agents. Induction of S100β expression has been documented in tissue of patients being treated with bronchodilator drugs such as phosphodiesterase inhibitors and β-adrenergic agonists for chronic lung disease. In these patients, S100β is expressed in the heart, skeletal muscle and kidney, tissues that normally express S100A1 but not S100β. It is possible that altered S100β expression is involved in the expression of toxic effects, as studies have shown that altered S100β expression occurs in response to toxicological agents such as hexane and perchloroethylene. Interestingly, a variety of bronchodilator-like substances including adrenergic agonists have been shown to increase BBB permeability. The observed changes in S100β in plasma of patients undergoing these therapies may therefore depend also on increased extravasation of S100β from CSF to serum via an impaired BBB.

Comparison of S100β changes with increased concentrations of other markers of neuronal damage. Because of the demonstration that considerable part of ischemic brain tissue does not immediately become necrotic, but succumbs to delayed degeneration, the rationale for hyper acute treatments aimed to restore perfusion and to protect neuronal tissue from necrosis has become evident. MRI/CT post-ischemic changes are usually not evident for many hours after infarction but early diagnosis by peripheral markers would be greatly beneficial for strategic planning of therapeutic interventions.

One of the more important aspects of the present invention is identification of a peripheral marker which is capable of differentiating between blood brain barrier permeability and neuronal damage. FIGS. 2 and 3 illustrate the expected release of proteins in the case of neuronal damage with intact blood brain barrier; neuronal damage and blood brain barrier opening; and blood brain barrier opening without neuronal damage. S100β is the preferred peripheral marker for BBB opening is because there is more S100β in the brain than in the blood under normal conditions. It is not necessary to have damage for production of S100β to have an increased concentration in plasma. All that is necessary is an opening of the barrier. The other markers by themselves are less than desirable peripheral markers for detecting an opening of the blood brain barrier because there is not a substantial difference between the amounts as present in the brain as present in the blood when there is no neuronal damage. They are, however, good markers of damage because their concentration goes very high in the brain after damage occurs. It should be noted that damage typically occurs at hours intervals, whereas S100β release will occur very rapidly (even as rapidly as seconds).

One important aspect of the present invention that is derived from the distinction of S100β availability and other CNS marker (e.g. NSE and GFAP) availability. The present invention allows for a substantially non-invasive determination of blood brain barrier permeability by peripheral detection of S100β. It is expected that S100β will be released very close in time to the opening of the blood brain barrier. Thus upon detection of S100β, other markers of brain damage may be utilized to determine the onset of neuronal distress or damage. As illustrated in FIG. 2 and FIG. 3, the present invention allows for discrimination of: opening without damage; opening with damage; and damage without opening (see FIG. 2). This is accomplished with detection of S100β, alone or in combination with other markers.

One particular useful aspect of the present invention is in chronic neurological disease, which over a period of time first manifests itself first by a release of S100β, and then release of other markers of neuronal distress (e.g. NSE). Thus, the present invention can be used to stage the progression of the disease. In chronic neurological diseases, where the BBB opens before the disease becomes, pathology, becomes apparent. An example may be Alzheimer's disease, multiple sclerosis, or other diseases where believed that the BBB opens before the symptoms occur. In these cases, it would be expected that S100β would be elevated in the plasma before markers of neuronal damage become elevated. If routine measurements or samples are taken, a peripheral increase in S100β should precede an increase in the other markers.

Another embodiment of the present invention is the differential diagnosis of tumors. In a metastatic tumor that originates in the periphery and grows into the brain, one would expect a marker of the tumor (e.g., prostate, breast, etc.), to be elevated. However, S100β will increase only when the tumor breaches the BBB, which is when the tumor becomes metastatic.

In a primary brain tumor patient, if a marker of the specific brain tumor is known, it will be released into the blood at the same time or substantially simultaneous as the BBB opens. This is due to the fact that if the tumor releases a marker that stays into the brain, one would not be able to measure it in plasma until the BBB is open. Even without the marker, S100β in the blood may be an indication of a primary tumor. The present invention may also have particular applicability in the detection of primary tumors, due to the fact that the vessels that feed the tumor do not have the BBB phenotype, and thus leakage of S100β into the blood is expected to occur when the tumor undergoes angiogenesis.

Another particularly useful aspect of the present invention would be in the reoccurrence of a primary brain tumor. Once a brain tumor is removed, it is expected that the tumor markers as well as markers of leakage of the BBB will go down. However, if the tumor surfaces again, leakage of S100β into the plasma will result in early detection of recurrence of a primary brain tumor.

The present invention allows for opening the BBB on command, and monitoring the status, as well as directing therapeutic agents to the brain while the BBB is open. The present invention provides methods for the diagnostic and prognostic evaluation of a subject's BBB to determine the status of a disease as well as to evaluate the susceptibility of the BBB to agents which require opening of the BBB to be therapeutic. The assays of the invention comprise methods designed to detect increased levels of S100β, protein, or the presence of S100β antibodies or autoantibodies, in serum or other biological fluids of a subject.

Specifically, the invention encompasses a method for diagnosis and prognosis of the BBB in a subject comprising: detecting a S100β protein in a biological fluid sample derived from a subject as is know in the art, with as little as 2–5 mL of the sample; and comparing the level of protein detected in the subject's sample to the level of protein detected in a control sample, wherein an increase in the level of S100β protein detected in the subject's sample as compared to control samples is an indicator of the degree to which the blood brain barrier has opened. If S100β is released as a consequence of neuronal damage and the BBB opening follows this event, measurable neuronal damage will precede temporal increases in S100β availability in plasma. If, conversely, BBB opening precedes neuronal damage the opposite will be true. Note however, that under the latter conditions two separate peaks of S100β concentration in plasma will be observed, one due to leakage across the BBB and an additional peak caused by massive release of S100β by suffering neuronal cells and glia. As pointed out above, extravasation of S100β in plasma also occurs in the absence of neuronal damage (see FIG. 2). This constitutes the basis of our invention. Under these conditions, it is assumed that S100β is readily available in the cerebral spinal fluid but not in plasma under normal conditions. Following opening of the BBB, even in the absence of any damage, S100β extravasates and becomes available in the plasma compartment.

Figure 4:
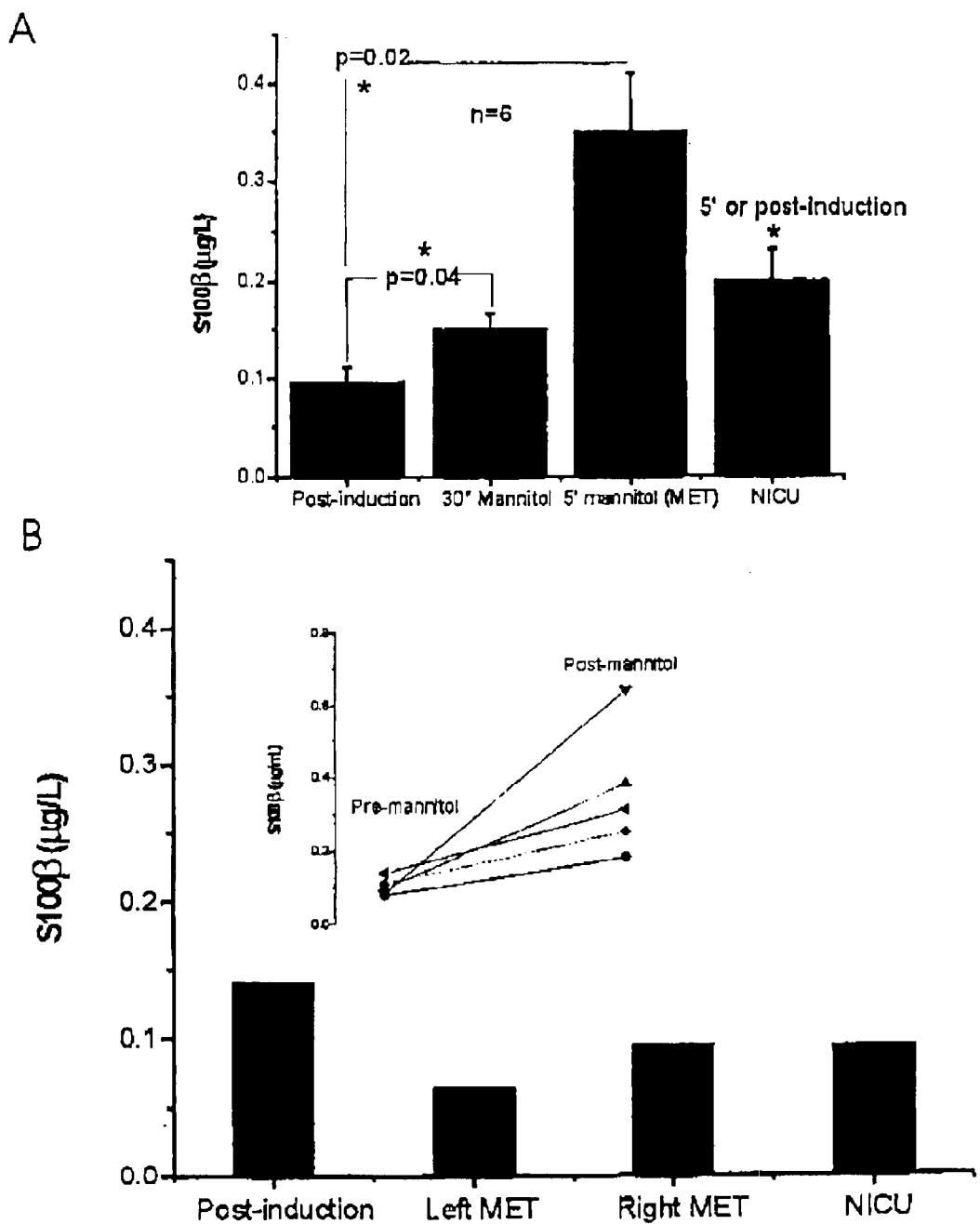
FIG. 4A is a bar graph of the S100β levels upon opening of the BBB with mannitol.
FIG. 4B is a bar graph of the S100β levels without administration of an agent to open the BBB.

FIG. 4 illustrates the hyperosmotic opening of the BBB reveals increases of plasma S100β. A 70 year old male suffering from bilateral brain lymphoma was treated by intra-arterial application of Methotrexate following opening of the BBB by hyperosmotic Mannitol. This procedure was originally described by Neuwelt, et al in "Outwitting the blood brain barrier for therapeutic purposes osmotic opening and other means." Kroll et al., Neurosurgery. 1998 May; 42(5): 1083, 1100, which is hereby incorporated by reference herein in its entirety. S100β levels were measured in plasma following induction of anesthesia, 30 seconds after injection of the intracarotid Mannitol, approximately 5 minutes after Mannitol injection and two minutes following Methotrexate injection. Finally, levels were also measured 24 hours after the procedure when the patient was recovering in the NICU. This procedure is repeated approximately monthly, on two separate days. On day 1, one hemisphere is injection and the following day a second procedure is applied to the contra lateral hemisphere. Note that 30 seconds after Mannitol injection a statistically significant increase of S100β in plasma was observed. This increase was more dramatic following additional time (five minutes). At this time, Methotrexate was also injected into the blood stream but appeared to have little effect on S100β levels when injected alone (see "B" in FIG. 4). S100β levels remained elevated during recovery time in the NICU and remained statistically elevated compared to post induction values, but were also significantly lower than those measured 5 minutes after Mannitol injection. NSE was also measured in this patient, and this did not change. Accordingly, the patient, as expected, does not have brain damage, but rather an opening in the BBB.

A control experiment was performed on a female 70 year old with a bilateral brain tumor. A 70 year old female was treated with intra arterial Methotrexate without previous opening of the BBB. Note that in this patient post induction levels were comparable to those measured in the patient shown in "a", but that following injection of Methotrexate in the left hemisphere and immediately afterwards to the right hemisphere did not significantly change S100β levels. These levels remained constant following recovery in the NICU also. These results are compared to those shown in the inset which depicts the effects of Mannitol+Methotrexate in five subsequent openings obtained for the patient shown in "a" (the male 70 year old). Note that S100β increased in every single experiment, suggesting that the BBB was opened by Mannitol.

Figure 5:
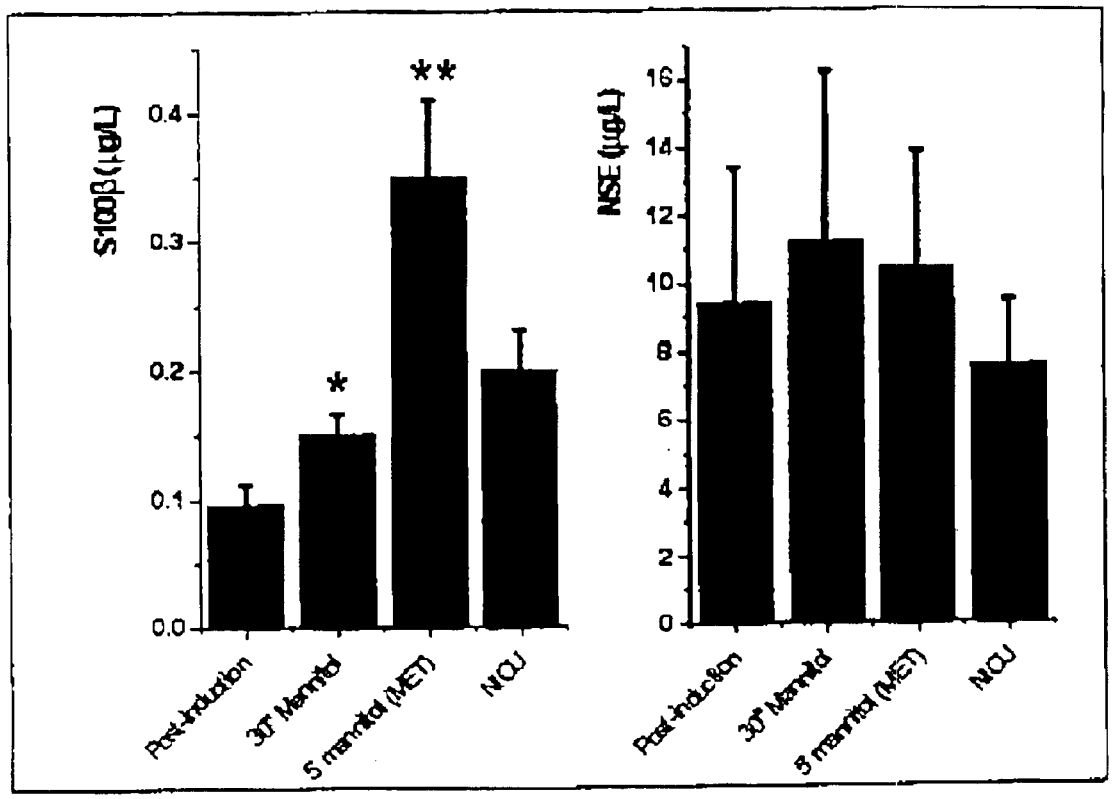
FIG. 5 illustrates the differentiation of BBB opening from neuronal damage.

FIG. 5 illustrates the differentiation of BBB opening from neuronal damage. Data was obtained from the same patient shown in FIG. 4a. The data in the left panel is identical to 4a, while the data in the right panel shows levels of NSE measured in the same samples used to determine S100β. Note that a sudden and progressive increase in S100β occurs following opening of the BBB with Mannitol while during the same time period the levels of neuron specific amylase remain constant.

The present invention encompasses a method for diagnosis and prognosis of a subject's BBB, comprising: contacting a serum sample derived from a subject with a sample containing S100β protein under conditions such that a specific antigen-antibody binding can occur; and detecting the presence of S100β present in the subject's serum, wherein the presence of immunospecific binding indicates level or degree to which the BBB is open.

In a specific embodiment of invention, the S100β protein is utilized to screen a subject's serum for the presence of S100β by means of sensitive and rapid immunoadsorbent assays or by other procedures. An assay that is commercially available which would be suitable if modified for use in the present invention is the Sangtec® 100 available from Sangtec Medical.

The present invention also provides for kits for carrying out the above described methods. The methods can be performed, for example, by utilizing prepackaged diagnostic kits comprising at least a reagent for detecting S100β protein such as an anti-S100β antibody. Alternatively, the diagnostic kits may comprise an S100β peptide for detection of S100β autoantibodies in a subject derived sample.

In accordance with the invention, measurement of levels of S100β proteins in serum or body fluids can be used for the early diagnosis of diseases associated with an open BBB, such as neurological disorders. Moreover, the monitoring of S100β protein levels can be used prognostically to stage the progression of the disease and to evaluate the efficacy of compounds in penetrating the BBB.

The detection of S100β proteins in a body fluid from a subject can be accomplished by any of a number of methods. Preferred diagnostic methods for the detection of S100β proteins in the serum of a patient can involve, for example, immunoassays wherein S100β proteins are detected by their interaction with an S100β specific antibody. Antibodies useful in the present invention can be used to quantitatively or qualitatively detect the presence of S100β peptides. In addition, reagents other than antibodies, such as, for example, polypeptides that bind specifically to S100β proteins can be used in assays to detect the level of S100β protein expression.

Immunoassays to be used in the practice of the invention include but are not limited to assay systems using techniques such as Western blots, radioimmunoassays, ELISA (enzyme linked immunosorbent assay),"sandwich" immunoassays, immunoprecipitation assays, precipitation reactions, gel diffusion precipitation reactions, immunodiffusion assays, agglutination assays, complement fixation assays, immunoradiometric assays, fluorescent immunoassays, protein A immunoassays, to name but a few.

A biological sample which may contain S100β proteins, such as serum or other biological fluids in which secreted proteins can localize, is obtained from a subject suspected of having a particular breach of the BBB or a patient in which it is desirable to open the BBB. Immunoassays for detecting expression of S100β protein typically comprise contacting the biological sample, such as a serum sample derived from a subject, with an anti-S100β antibody under conditions such that specific antigen-antibody binding can occur, and detecting or measuring the amount of any immunospecific binding by the antibody. In a specific aspect, such binding of antibody, for example, can be used to detect the presence and increased expression of S100β proteins wherein the detection of increased expression of S100β proteins is an indication of a diseased condition. The levels of S100β protein in a serum sample are compared to norms established for normal individuals and for subjects at a variety of stages of BBB integrity or opening.

In an embodiment of the invention, the biological sample, such as a serum sample is brought in contact with a solid phase support or carrier, such as nitrocellulose, for the purpose of immobilizing any proteins present in the sample. The support is then washed with suitable buffers followed by treatment with detectably labeled S100β specific antibody. The solid phase support is then washed with the buffer a second time to remove unbound antibody. The amount of bound antibody on the solid support is then determined according to well known methods.

One of the ways in which S100β antibodies can be detectably labeled is by linking the antibody to an enzyme, such as for use in an enzyme immunoassay (EIA) (Voller, A., "The Enzyme Linked immunosorbent Assay (ELISA)", 1978, Diagnostic Horizons 2: 1–7, Microbiological Associates Quarterly Publication, Walkersville, Md.; Voller, A., et al., 1978, J. Clin. Pathol. 31: 507–520; Butler, J. E., 1981, Meth. Enzymol. 73: 482–523). The enzyme which is bound to the antibody will react with an appropriate substrate, preferably a chromogenic substrate, in such a manner as to produce a chemical moiety that can be detected, for example, by spectrophotometric, fluorimetric, or by visual means. Enzymes that can be used to detectable label the antibody include, but are not limited to, horseradish peroxidase and alkaline phosphatase. The detection can also be accomplished by calorimetric methods that employ a chromogenic substrate for the enzyme.

Detection of S100β antibodies may also be accomplished using a variety of other methods. For example, by radioactively labeling the antibodies or antibody fragments, it is possible to detect S100β protein expression through the use of a radioimmunoassay (RIA) (see, for example., Weintraub, B., Principles of Radioimmunoassays, Seventh Training Course on Radioligand Assay Techniques, The Endocrine Society, March 1986). The radioactive isotope can be detected by such means as the use of a gamma counter or a scintillation counter or by autoradiography.

The antibody may also be labeled with a fluorescent compound. Among the most commonly used fluorescent labeling compounds are fluorescein isothiocyanate rhodamine, phycoerythrin and fluorescamine. Likewise, a bioluminescent compound may be used to label the S100β antibody. The presence of a bioluminescence protein is determined by detecting the presence of luminescence. Important bioluminescence compounds for purposes of labeling are luciferin, luciferase and aequorin.

Expression levels of S100β proteins in biological samples can be analyzed by two-dimensional gel electrophoresis. Methods of two-dimensional electrophoresis are known to those skilled in the art. Biological samples, such as serum samples, are loaded onto electrophoretic gels for isoelectric focusing separation in the first dimension which separates proteins based on charge. A number of first-dimension gel preparations may be utilized including tube gels for carrier ampholytes-based separations or gels strips for immobilized gradients based separations. After first-dimension separation, proteins are transferred onto the second dimension gel, following an equilibration procedure and separated using SDS PAGE which separates the proteins based on molecular weight. When comparing serum samples derived from different subjects, multiple gels are prepared from individual serum samples.

Following separation, the proteins are transferred from the two dimensional gels onto membranes commonly used for Western blotting. The techniques of Western blotting and subsequent visualization of proteins are also well known in the art (Sambrook et al, "Molecular Cloning, A Laboratory Manual", $2^{nd}$ Edition, Volume 3, 1989, Cold Spring Harbor). The standard procedures may be used, or the procedures may be modified as known in the art for identification of proteins of particular types, such as highly basic or acidic, or lipid soluble, etc. (See for example, Ausubel, et al., 1989, Current Protocols in Molecular Biology, Green Publishing Associates and Wiley Interscience, N.Y.). Antibodies that bind to the S100β proteins are utilized in an incubation step, as in the procedure of Western blot analysis. A second antibody specific for the first antibody is utilized in the procedure of Western blot analysis to visualize proteins that reacted with the first antibody.

The detection of S100β protein expression can also be used to monitor the efficacy of potential anti-cancer compounds during treatment. For example, the level of S100β protein expression can be determined before and during treatment. The efficacy of the compound can be followed by comparing S100β expression throughout the treatment to ensure that the BBB is open and receptive to the chemotherapeutic agents.

The immunoassays can be conducted in a variety of ways. For example, one method to conduct such assays involves anchoring of S100β protein onto a solid support and detecting anti-S100β antibodies specifically bound thereto. The S100β proteins to be utilized in the assays of the invention can be prepared via recombinant DNA techniques well known in the art. For example, in instances where the nucleotide sequence of a DNA encoding an S100β protein is available, the DNA can be genetically engineered into an appropriate expression vector for large scale preparation of S100β protein. It may be advantageous to engineer fusion proteins that can facilitate labeling, immobilization or detection of the S100β protein. See, for example, the techniques described in Sambrook et al., 1989, Molecular Cloning: A laboratory Manual, Cold Spring Harbor Press, Cold Spring Harbor, N.Y.

Alternatively, the S100β protein may be purified from natural sources, e.g., purified from cells, using protein separation techniques well known in the art. Such purification techniques may include, but are not limited to molecular sieve chromatography and/or ion exchange chromatography. In practice, microtitre plates are conveniently utilized as the solid support for the S100β proteins. The surfaces may be prepared in advance and stored.

Those skilled in the art will be able to determine optional assay conditions for each determination by employing routine experimentation.

KITS. The present invention further provides for kits for carrying out the above-described assays. The assays described herein can be performed, for example, by utilizing pre-packaged diagnostic kits, comprising at least an S100β peptide (for detection of S100β or S100β autoantibodies) or an S100β antibody reagent (for detection of S100β protein), which can be conveniently used, e.g., in clinical settings to diagnose the degree or state of the BBB.

In a first series of nonlimiting embodiments, a kit according to the invention comprises components for detecting and/or measuring human IgG antibodies directed toward S100β antigen. As one example, where the antibodies are detected and/or measured by enzyme linked immunoabsorbent assay (ELISA), such components may comprise target antigen, in the form of at least one and preferably a plurality of different S100β antigens or epitopes thereof, linked to a solid phase, and a means for detecting a human antibody antibody bound to target antigen. Such means for detection may be, for example, an antibody directed toward the constant region of human IgG (e.g., rabbit antihuman IgG antibody), which may itself be detectably labeled (e.g., with a radioactive, fluorescent, colorimetric or enzyme label), or which may be detected by a labeled secondary antibody (e.g., goat anti-rabbit antibody).

In a second series of nonlimiting embodiments, a kit according to the invention may comprise components which detect and/or measure S100β antigens in the biological sample of a subject. For example, where S100β proteins are detected and/or measured by enzyme linked immunoabsorbent assay (ELISA), such components may comprise an antibody directed to epitopes of the S100β proteins which can be used to detect and/or quantitate the level of S100β expression in the biological sample. The antibody itself may be detectably labeled with a radioactive, flourescent, calorimetric or enzyme label. Alternatively, the kit may contain a labeled secondary antibody. S100β kits which can be modified in accordance with the present invention are available from commercial suppliers such as Sangtec Medical, and are known as Sangtec®100.

Further aspects of the invention provide methods as described above of monitoring the level of permeability of the BBB. This is particularly useful when following a treatment course wherein the treatment course includes opening of the BBB. Compounds which typically have trouble passing through the blood brain barrier, where the compounds administered into the patient's bloodstream include, by way of nonlimiting example, any of neuropharmacologic agents, neuroactive peptides (e.g., hormones, gastrointestinal peptides, angiotensin, sleep peptides, etc.), proteins (e.g, calcium binding proteins), enzymes (e.g., cholineacetyltransferase, glutamic acid decarboxylase, etc.), gene therapy agents, neuroprotective or growth factors, biogenic amines (e.g., dopamine, GABA), trophic factors to brain or spinal transplants, immunoreactive proteins (e.g, antibodies to neurons, myelin, antireceptor antibodies), receptor binding proteins (e.g., opiate receptors), radioactive agents (e.g., radioactive isotopes), antibodies, and cytotoxins, among others.

Related aspects of the invention provide methods for treating neurological disorders by monitoring the permeability of the compounds through the blood brain barrier in accord with the methods described above. Such disorders include tumors, cancer, degenerative disorders, sensory and motor abnormalities, seizure, infection, immunologic disorder, mental disorder, behavioral disorder, and localized CNS disease, among others.

In still further related aspects, the invention provides methods for modification of neurologic and neurologically-related activity (e.g., behavioral activity, memory-related activity, and sexual activity, among others) by such methods.

In still further related aspects, the invention provides methods for modification of neurologic and neurologically-related activity (e.g., behavioral activity, memory-related activity, and sexual activity, among others) by such methods.

All of the embodiments disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The following references, to the extent that they provide exemplary procedural or other details supplementary to those set forth herein, are specifically incorporated herein by reference.

What is claimed is:

1. A method for diagnosis of blood brain barrier permeability in a subject comprising:
    detecting a first elevated level of S100β in the blood of a patient;
    identifying a second elevated level of S100β in the blood of the patient after said first elevated level of S100β is detected; and
    comparing first and second elevated levels of S100β wherein a statistically relevant first level of S100β protein is indicative of blood brain barrier permeability without neuronal damage and a second elevated level of S100β is indicative of neuronal damage.

2. The method of claim 1, wherein the second elevated level of S100β has a value which is greater than said value of first elevated level of S100β.

3. The method of claim 1, wherein said value of said second elevated level of S100β is greater than twice the value of said first elevated level of S100β.

4. The method of claim 1, wherein said value of said first elevated level S100β is in the range of about 0.12 ng/ml to 0.35 ng/ml.

5. The method of claim 1, wherein said value of said second elevated level of S100β is in the range of about 0.35 ng/ml.

6. A method for diagnosis of blood brain barrier permeability in a subject comprising:

detecting a first elevated level of S100β in the blood of a patient, said first level of S100β being indicative of blood brain barrier permeability without neuronal damage; and identifying a second elevated level of S100β in the blood of the patient after said first elevated level of S100β is detected, the second elevated level of S100β having a value greater than said value of said first elevated level of S100β.

7. The method of claim 6, wherein said value of said second elevated level of S100β is indicative of neuronal damage.

8. The method of claim 6, wherein said value of said second elevated level of S100β is greater than twice the value of said first elevated level of S100β.

9. The method of claim 8, where wherein said value of said second elevated level of S100β is indicative of neuronal damage.

10. The method of claim 6, wherein said value of said first elevated level of S100β is in the range of about 0.12 ng/ml to 0.35 ng/ml.

11. The method of claim 6, wherein said value of said second level of S100β is in the range of about 0.35 ng/ml.

12. The method of claim 6, wherein the first elevated level of S100β is detected using an immunoassay.

13. The method of claim 6, wherein the second elevated level of S100β is detected using an immunoassay.

14. The method of claim 12, wherein the immunoassay is an immunoprecipitation assay.

15. The method of claim 13, wherein the immunoassay is an immunoprecipitation assay.

16. The method of claim 6, further comprising detecting levels of NSE and GFAP.

17. A method for diagnosis of blood brain barrier permeability in a subject comprising:

detecting a first elevated level of S100β in the blood of a patient, wherein said first level of S100β has a value of about 0.12 ng/ml to about 0.35 ng/ml;

identifying a second elevated level of S100β in the blood of the patient; and comparing first and second elevated levels of S100β wherein a statistically relevant first level of S100β protein is indicative of blood brain barrier permeability without neuronal damage and a second elevated level of S100β is indicative of neuronal damage.

18. The method of claim 17, wherein the second elevated level of S100β has a value which is greater than said value of first elevated level of S100β.

19. The method of claim 17, wherein said value of said second elevated level of S100β is greater than twice the value of said first elevated level of S100β.

20. The method of claim 17, wherein said value or said second elevated level of S100β is in the range of about 0.35 ng/ml.

21. A method for diagnosis of blood brain barrier permeability in a subject comprising:

detecting a first elevated level of S100β in the blood of a patient, wherein said first level of S100β has a value of about 0.12 ng/ml to about 0.35 ng/ml, wherein said first level of S100β being indicative of blood brain barrier permeability without neuronal damage; and identifying a second elevated level of S100β in the blood of the patient, the second elevated level of S100β having a value greater than said value of said first elevated level of S100β.

22. The method of claim 21, wherein said value of said second elevated level of S100β is indicative of neuronal damage.

23. The method of claim 21, wherein said value of said second elevated level of S100β greater than twice the value of said first elevated level of S100β.

24. The method of claim 21, wherein said value of said second level of S100β is in the range of about 0.35 ng/ml.

25. The method of claim 21, wherein the first elevated level of S100β is detected using an immunoassay.

26. The method of claim 21, wherein the second elevated level of S100β is detected using an immunoassay.

27. The method of claim 25, wherein the immunoassay is an immunoprecipitation assay.

28. The method of claim 25, wherein the immunoassay is an immunoprecipitation assay.

29. The method of claim 21, further comprising detecting levels of NSE and GFAP.

* * * * *